(12) United States Patent
Bacchetta et al.

(10) Patent No.: US 11,291,747 B2
(45) Date of Patent: Apr. 5, 2022

(54) CELL-SEEDED POROUS LUNG HYDROGEL SEALANT

(71) Applicant: The Trustees of Columbia University in the City of New York, New York, NY (US)

(72) Inventors: Matthew Bacchetta, Tenafly, NJ (US); Brandon Guenthart, New York, NY (US); Jinho Kim, Jersey City, NJ (US); John O'Neill, New York, NY (US); Gordana Vunjak-Novakovic, New York, NY (US)

(73) Assignee: The Trustees of Columbia University in The City of New York, New York, NY (US)

( * ) Notice: Subject to any disclaimer, the term of this patent is extended or adjusted under 35 U.S.C. 154(b) by 0 days.

(21) Appl. No.: 16/371,703

(22) Filed: Apr. 1, 2019

(65) Prior Publication Data
US 2019/0224364 A1    Jul. 25, 2019

Related U.S. Application Data

(63) Continuation of application No. PCT/US2017/055549, filed on Oct. 6, 2017.

(60) Provisional application No. 62/404,991, filed on Oct. 6, 2016.

(51) Int. Cl.
*A61L 24/00* (2006.01)
*A61L 24/04* (2006.01)
*A61L 24/10* (2006.01)

(52) U.S. Cl.
CPC ....... *A61L 24/0031* (2013.01); *A61L 24/0005* (2013.01); *A61L 24/0036* (2013.01); *A61L 24/043* (2013.01); *A61L 24/102* (2013.01); *A61L 24/104* (2013.01); *A61L 24/108* (2013.01); *A61L 24/0094* (2013.01)

(58) Field of Classification Search
None
See application file for complete search history.

(56) References Cited

U.S. PATENT DOCUMENTS

| | | | |
|---|---|---|---|
| 5,895,412 A | 4/1999 | Tucker | |
| 6,183,498 B1 | 2/2001 | Devore et al. | |
| 6,352,710 B2 | 3/2002 | Sawhney et al. | |
| 9,238,090 B1 * | 1/2016 | Fette | A61L 27/3633 |
| 2005/0069589 A1 | 3/2005 | Lowinger et al. | |
| 2007/0225631 A1 | 9/2007 | Bowlin et al. | |
| 2008/0107708 A1 | 5/2008 | Ng et al. | |
| 2008/0305517 A1 | 12/2008 | Griffin et al. | |

(Continued)

FOREIGN PATENT DOCUMENTS

WO    2009153748 A3    12/2009

OTHER PUBLICATIONS

Chrzanowski et al (Abstract for "Elastin content of normal and emphysematous lung parenchyma", The American Journal of Medicine, vol. 69(3), p. 351-359 (1980)). (Year: 1980).*

(Continued)

*Primary Examiner* — Sin J Lee
(74) *Attorney, Agent, or Firm* — Reed Smith LLP; Lisa A. Chiarini; Walter M. Egbert, III

(57) ABSTRACT

Disclosed are a biosealant system and method for treatment of a pulmonary air leak comprising applying the biosealant system to the locus of the air leak.

26 Claims, 7 Drawing Sheets

(56) References Cited

U.S. PATENT DOCUMENTS

| | | |
|---|---|---|
| 2009/0142396 A1 | 6/2009 | Odar et al. |
| 2010/0063459 A1 | 3/2010 | Preiss-Bloom et al. |
| 2011/0112573 A1 | 5/2011 | Bloom |
| 2012/0128749 A1 | 5/2012 | Tsuji et al. |
| 2012/0288474 A1* | 11/2012 | Kungl ............... C07K 14/5421 424/85.2 |
| 2014/0220130 A1 | 8/2014 | Larsen et al. |
| 2015/0037434 A1 | 2/2015 | Freytes et al. |
| 2016/0030635 A1 | 2/2016 | Bhatia et al. |

OTHER PUBLICATIONS

International Search Report and Written Opinion cited in corresponding International Application No. PCT/US2017/055549 dated Dec. 28, 2017.
Chen et al. "High Glucose Alters Proteoglycan Expression and the Glycosaminoglycan Composition in Placentas of Women with Gestational Diabetes Mellitus and in Cultured Trophoblasts" Placenta, 2007; 28(2-3):97-106 (doi: 10.1016/j.placenta.2006.02.009) p. 98, col. 1, para 1.
C. Elvin et al., "A highly elastic tissue sealant based on photopolymerised gelatin", Biomaterials, vol. 31/ Issue 32 pp. 8323-8331, Nov. 2010.
P. Charron et al., "Mechanical properties and failure analysis of visible light crosslinked alginate based tissue sealants", Journal of the Mechanical Behavior of Biomedical Materials, vol. 59, pp. 314-321, Jun. 2016.
Y. Otani et al., "Sealing effect of rapidly curable gelatin-poly (L-glutamic acid) hydrogel glue on lung air leak", Annals of Thoracic Surgery, vol. 67/Issue 4, pp. 922-926, Apr. 1999.
Y. Liu et al., "Biomimetic sealant based on gelatin and microbial transglutaminase: an initial in vivo investigation", Journal of biomedical Materials Research Part B, vol. 91B/ Issue 1, pp. 5-16, Oct. 2009.
G. McDermott et al., "Mechanical properties of biomimetic tissue adhesive based on the microbial transglutaminase-catalyzed crosslinking of gelatin", Biomacromolecules, vol. 5/ Issue 4, pp. 1270-1279, Apr. 2004.

* cited by examiner

401

CELL-SEEDED POROUS LUNG HYDROGEL SEALANT

CROSS-REFERENCE TO RELATED APPLICATIONS

The present application is a continuation of International Application PCT/US2017/055549, filed on Oct. 6, 2017, which claims priority to U.S. Provisional Application No. 62/404,991, filed Oct. 6, 2016, both of which are herein incorporated by reference in their entirety.

FIELD OF THE DISCLOSED SUBJECT MATTER

The subject matter pertains to a sealant for treating pulmonary air leaks.

BACKGROUND OF THE DISCLOSED SUBJECT MATTER

Patients with prolonged air leaks (greater than seven days duration), such as from septum rupture, following lung resection often suffer prolonged hospitalization (up to weeks) and are most commonly managed with tube thoracostomy (i.e., a chest tube placed into the thoracic cavity to drain air/fluid while the lung heals). Patients that fail this first-line therapy are often taken back to the operating room for further intervention. Another option in the treatment of prolonged air leaks are endobronchial valves; however they often have little effect and are prone to complications (e.g., dislodgment, inflammation, infection).

Air leaks occur in 15-18% of patients undergoing lung resection. There is a critical need in the field to prevent this complication, improve patient care, and decrease cost. Additionally, patients with underlying lung disease (e.g., COPD, emphysema) are more likely to suffer from air leaks following any intervention (e.g., surgery, IR biopsy) and other processes such as trauma can cause damage to the lung parenchyma, leading to air leaks. There is also a substantial need to treat these patients.

Physical adhesive patches over the air leak have been used as an alternative option. Such patches include synthetic self-adhesive sealant and barrier functions. Also known are two-part systems that form an adhesive patch over the air leak, including polyethylene glycol/human serum albumin, albumin/glutaraldehyde, or thrombin/fibrinogen combinations.

The solutions listed above are mainly fibrin-based products originally designed as adhesives for other applications in the body. Their adhesive and mechanical properties are not well-suited for the complex dynamics of the lung, and they are unable to accommodate mechanical changes in the lung during ventilation. They serve as very poor sealants and contain no organ- or tissue-specificity in properties or composition. Many rely on hemostatic mechanisms (e.g., activation in the presence of bleeding which is not present on the pleural surface of the lung). Metaanalysis data has shown little evidence that any of these products are effective in reducing air leaks, length of hospital stay, or cost. As a result, there is no routine use of any lung sealant today.

Thus, there is a continuing need for an effective lung sealant that can be used to treat pulmonary air leaks to avoid more costly surgical procedures.

SUMMARY OF THE DISCLOSED SUBJECT MATTER

The present disclosure is directed to a biosealant composition.

In one embodiment, the biosealant composition comprises an extracellular matrix hydrogel and a thermogel. The extracellular matrix hydrogel comprises a first extracellular matrix protein, an unbranched polysaccharide, and an elastic protein. The thermogel comprises gelatinous material and a cross-linking enzyme in an amount sufficient to result in gelation of the thermogel at a temperature from about 35° C. to 37° C.

In another embodiment, the biosealant composition comprises an extracellular matrix hydrogel as a first layer and a thermogel as a second layer, with the second layer is atop the first layer. The extracellular matrix hydrogel layer comprises collagen, sulfated glycosaminoglycan, and elastin. The thermogel comprises gelatin and transglutaminase.

In another embodiment, the biosealant composition comprises a first extracellular matrix protein; an unbranched polysaccharide; and an elastic protein; a gelatinous material; and a cross-linking enzyme.

In another embodiment, the biosealant composition comprises collagen, sulfated glycosaminoglycan, elastin, gelatin and transglutaminase.

The present disclosure is also directed to a method for sealing a puncture.

In one embodiment, the method comprises the steps of applying an extracellular matrix hydrogel to a puncture, where the extracellular matrix comprises a first extracellular matrix protein, an unbranched polysaccharide, and an elastic protein. The method then comprises the step of applying a thermogel on top of the extracellular matrix hydrogel, where the thermogel comprises a gelatinous material and a cross-linking enzyme, wherein the cross-linking agent is in an amount sufficient to result in gelation of the thermogel at a temperature from about 35° C. to 37° C.

In another embodiment, the method comprises the step of applying a composition to a puncture, where the composition comprises an extracellular matrix hydrogel and a thermogel. The extracellular matrix comprises a first extracellular matrix protein, an unbranched polysaccharide, and an elastic protein. The thermogel comprises a gelatinous material and a cross-linking enzyme in an amount sufficient to result in gelation of the thermogel at a temperature from about 35° C. to 37° C.

The present disclosure is also directed to a kit for sealing of a puncture.

In one embodiment, the kit comprises a first, second, and third component. The first component is a first extracellular matrix protein, an unbranched polysaccharide, and an elastic protein. The second component is a gelatinous material. The third component is a cross-linking enzyme.

The present disclosure is also directed to a method of making a biosealant.

In one embodiment, the method comprises the steps of mixing a first extracellular matrix protein, an unbranched polysaccharide, an elastic protein, and a cross-linking enzyme to form an extracellular matrix hydrogel, mixing a gelatinous material in saline with the cross-linking enzyme to form a thermogel, heating the thermogel to about 52° C. to 55° C.; and making the thermogel porous.

In any of the above embodiments, the first extracellular matrix protein of the extracellular matrix hydrogel is present in an amount from about 25% by weight to about 75% by weight of the total weight of the first extracellular matrix protein, unbranched polysaccharide, and elastic protein of the extracellular matrix hydrogel.

In any of the above embodiments, the unbranched polysaccharide of the extracellular matrix hydrogel is present in an amount from about 0.5% by weight to about 15% by weight of the total weight of the first extracellular matrix protein, unbranched polysaccharide, and elastic protein of the extracellular matrix hydrogel.

In any of the above embodiments, the elastic protein of the extracellular matrix hydrogel is present in an amount from about 25% to about 75% by weight of the total weight of the first extracellular matrix protein, unbranched polysaccharide, and elastic protein of the extracellular matrix hydrogel.

In any of the above embodiments, the first extracellular matrix protein of the extracellular matrix hydrogel is present in an amount from about 25% by weight to about 75% by weight of the total weight of the first extracellular matrix protein, unbranched polysaccharide, and elastic protein of the extracellular matrix hydrogel, the unbranched polysaccharide of the extracellular matrix hydrogel is present in an amount from about 0.5% by weight to about 15% by weight of the total weight of the first extracellular matrix protein, unbranched polysaccharide, and elastic protein of the extracellular matrix hydrogel, and the elastic protein of the extracellular matrix hydrogel is present in an amount from about 25% to about 75% by weight of the total weight of the first extracellular matrix protein, unbranched polysaccharide, and elastic protein of the extracellular matrix hydrogel.

In any of the above embodiments, the first extracellular matrix protein is collagen.

In any of the above embodiments, the unbranched polysaccharide is sulfated glycosaminoglycan.

In any of the above embodiments, the elastic protein is elastin.

In any of the above embodiments, the first extracellular matrix protein, an unbranched polysaccharide, and an elastic protein of the extracellular matrix hydrogel are derived from lung extracellular matrix.

In any of the above embodiments, the extracellular matrix hydrogel also comprises a cross-linking enzyme.

In any of the above embodiments, the extracellular matrix hydrogel also comprises a cross-linking enzyme in a concentration of 0.5 units/mL to 5 units/mL.

In any of the above embodiments, the cross-linking enzyme is transglutaminase.

In any of the above embodiments, the extracellular matrix hydrogel also comprises additional therapeutics including cells, microsomes, peptides, or drugs.

In any of the above embodiments, the gelatinous material of the thermogel is present in an amount from about 5% by weight to 10% by weight of the total weight of the thermogel.

In any of the above embodiments, the cross-linking enzyme of the thermogel is present in an amount from about 0.5 units/mL to 5 units/mL.

In any of the above embodiments, the gelatinous material is gelatin.

In any of the above embodiments, the thermogel further comprises one or more of the first extracellular matrix protein, the unbranched polysaccharide, and the elastic protein.

In any of the above embodiments, the first extracellular matrix protein of the thermogel is collagen.

In any of the above embodiments, the unbranched polysaccharide of the thermogel is sulfated glycosaminoglycan.

In any of the above embodiments, the elastic protein of the thermogel is elastin.

In any of the above embodiments, the first extracellular matrix protein, an unbranched polysaccharide, and an elastic protein of the thermogel are derived from lung extracellular matrix.

In any of the above embodiments, the thermogel comprises pores of diameter of about 0.025 mm to 90 mm.

In any of the above embodiments, the biosealant composition does not contain fibrin.

In any of the above embodiments, the first extracellular matrix protein is collagen, wherein the unbranched polysaccharide is sulfated glycosaminoglycan, and wherein the elastic protein is elastin.

In any of the above embodiments, the gelatinous material is gelatin, and wherein the cross-linking enzyme is transglutaminase.

In any of the above embodiments, the extracellular matrix hydrogel is applied directly to tissue.

In any of the above embodiments, the extracellular matrix hydrogel is applied directly to the surface of the lung.

In any of the above embodiments, the extracellular matrix hydrogel is applied directly to the surface of the lung by chest tubes, drainage catheters, or injection when the thoracic cavity is closed.

In any of the above embodiments, the extracellular matrix hydrogel is applied at the time of bronchoscopy within the airways via catheter.

In any of the above embodiments, the extracellular matrix hydrogel is applied directly to the surface of an extracorporeal lung.

In any of the above embodiments, the thermogel is made porous by bubbling gas with a bubble generator through the thermogel material.

BRIEF DESCRIPTION OF THE DRAWINGS AND FIGURES

DETAILED DESCRIPTION OF THE DISCLOSED SUBJECT MATTER

Figure 1:
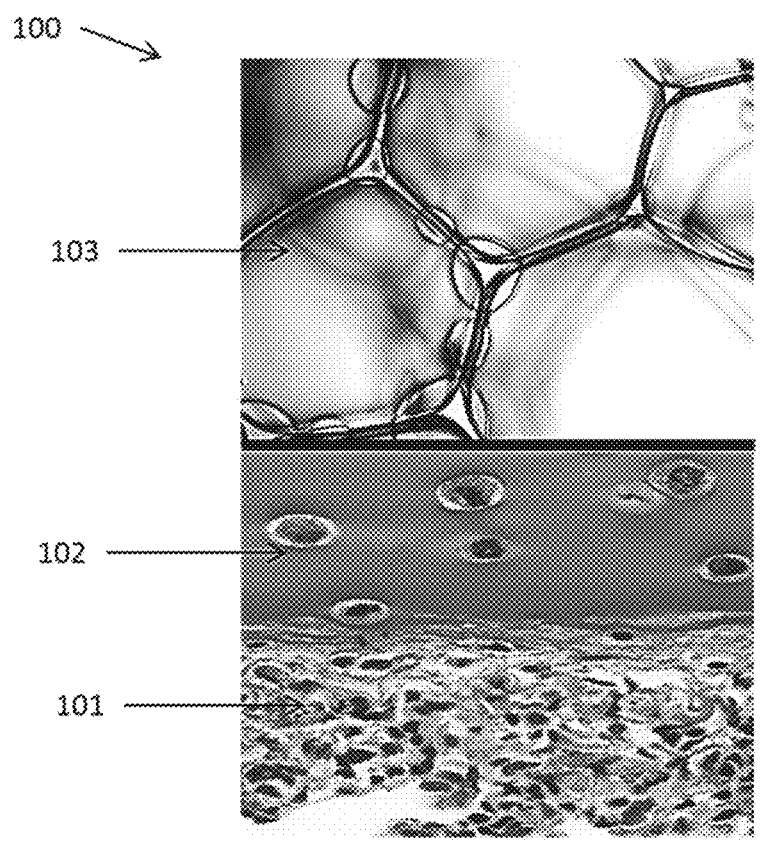
FIG. 1 shows photographic images used to show schematically the layers of the biosealant system.

There is a significant unmet clinical need and opportunity for the prevention and treatment of pulmonary air leaks. A biosealant product that could be applied at the time of surgery to prevent air leaks from occurring could result in decreased hospitalization, lower costs, less pain and fewer interventions on behalf of the patient. In addition to the prophylactic use of such a product, it could also be used to treat lung damage and air leaks occurring after surgery, trauma, or those known to occur spontaneously.

In accordance with the disclosed subject matter, a biomechanically compliant, loadable lung biosealant for the prevention and treatment of pulmonary air leaks is described. The biosealant is multi-layered, with a tissue-specific (e.g., lung parenchymal- or pleural-derived) extracellular matrix hydrogel carrier loaded with therapeutic cells, microsomes (e.g., exosomes, liposomes), peptides (e.g., growth factors), or drugs applied directly to the lung surface.

The sealant adheres effectively to the surface of lung by natural peptide-peptide interactions (e.g., proteinaceous components of lung biosealant with proteinaceous components of lung pleural or exposed lung parenchyma. The novel, biomimetic design that underlies the biocompatibility, sealing function, and mechanics of this lung biosealant relies on both the presence of native lung matrix biomolecules (collagen, sulfated glycosaminoglycans, and elastin) and the spongey and porous structure. The extracellular matrix biomolecules function to mimic the natural tissue architecture and mechanical properties of the lung and also ensure a vehicle for natural, biological, cytocompatible therapeutic payloads including drugs, cells, or cellular products like growth factors or other paracrine signals. While the composition of the lung matrix biomolecules in the sealant closely mimics natural lung composition, the lung matrix biomolecules are not necessarily derived directly from lung tissue. The spongey and porous structure of the biosealant is biomimetic—it recapitulates the natural spongey and porous structure of pulmonary alveoli (air sacs). This rational design feature is novel and unlike any other lung sealant device or material, and is one key to the effective sealing action of the biosealant.

EXAMPLES

The present invention is demonstrated in the following examples, it being understood that these are for illustrative purposes only, and the invention is not intended to be limited thereto.

Materials & Methods

Extracellular Matrix Hydrogel. The extracellular matrix components can be prepared in a concentrated liquid solution according to the following ranges: collagen: 80-120 µg/mg biosealant; sulfated glycosaminoglycans: 2-20 µg/mg biosealant; elastin: 50-250 µg/mg biosealant. The extracellular matrix hydrogel may also contain a cross-linking enzyme. This enzyme may be transglutaminase (0.5-5 units/mL), which is mixed with extracellular matrix components to obtain a extracellular matrix hydrogel.

Thermogel. The thermogel can be prepared by mixing 5-10% wt gelatin in normal saline, adding 0.5-5 unit/mL transglutaminase, and heating to 52-55° C. The resulting viscous thermogel material can then be made porous by bubbling gas (air) with a bubble generator through the thermogel material at 52-55° C. The gas is introduced into the bubble generator at a flow rate resulting in thermogel pores with diameter range of 25-500 µm, importantly approximately consistent with the range of diameters of ventilating pulmonary alveoli (air sacs), thus mimicking native lung structure and mechanics.

Application of Extracellular Matrix Hydrogel Layer and Thermogel Layer to Lung. Extracellular matrix hydrogel is applied to the surface of the lung. Then, porous thermogel is cooled to 37-42° C. and then applied to the lung over the previously applied lung extracellular matrix hydrogel. The specified ranges of gelatin and transglutaminase enable natural gelation (setting) of the thermogel at a range of 35-37° C. Following application onto the surface of the lung, gelation of the hydrogel layers occurs within 10-120 seconds (depending on the precise ratios of the multiple components described above). The final size (i.e., surface area) of the lung biosealant must be applied to an area at least 50% larger than the injured or ruptured area of the lung pleura.

Method of Application of Biosealant to Lung. Biosealant can be applied onto the surface of the lung at the time of open surgery (direct visualization) or minimally invasive surgery (video assisted) via 12-20 gauge applicators. Alternatively, the biosealant can be applied onto the surface of the lung with the chest closed through chest tubes or drainage catheters within the thoracic cavity, or injected with the aid of image guidance (e.g., computed tomography or ultrasound) onto the surface of the lung (12-20 gauge needles). Alternatively, the biosealant can be injected at the time of bronchoscopy within the airways via a catheter 1.5-2 mm in diameter. Alternatively, the biosealant can be applied directly onto the surface of an extracorporeal lung (i.e., lung supported outside the body with ex vivo lung perfusion) via 12-20 gauge applicators.

Example 1

FIG. 1 depicts the thermogel and extracellular matrix hydrogel components of the biosealant system. The photographs are not necessarily to the same scale. The biosealant system 100 comprises an extracellular matrix hydrogel layer 102 applied directly to the lung surface 101. Proximate the extracellular matrix hydrogel layer 102 is the porous thermogel layer 103.

Figure 2A:
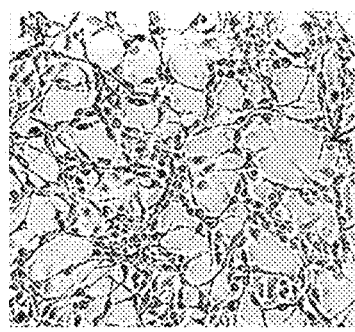
FIGS. 2A-2F show aspects of the extracellular matrix hydrogel layer.
Figure 2B:
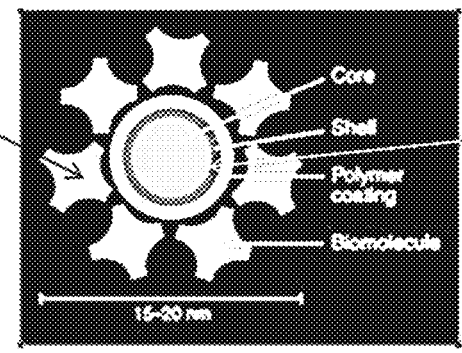
Figure 2C:
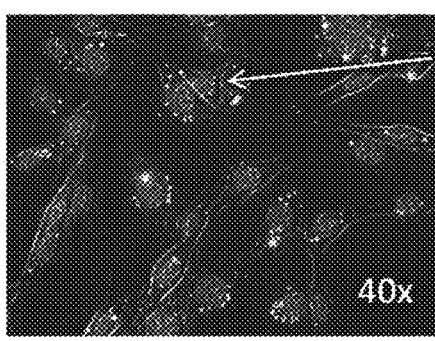
Figure 2D:
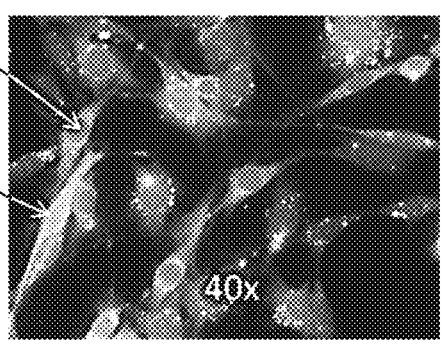
Figure 2F:
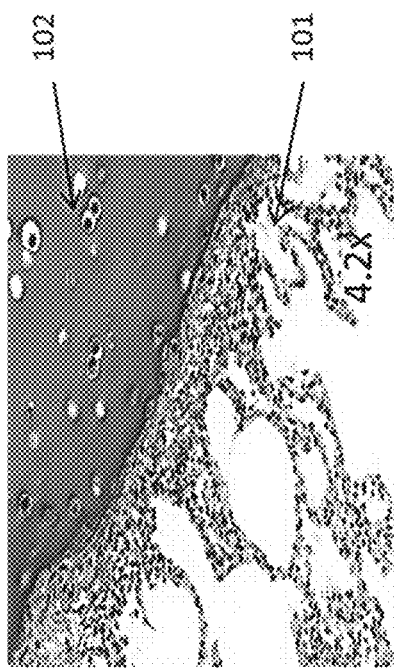
Figure 2E:
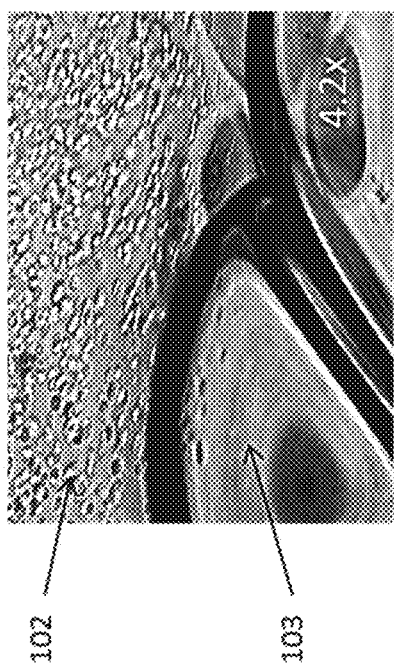

Referring to FIGS. 2A-2F aspects of the extracellular matrix hydrogel layer are depicted. As shown in FIG. 2A, a loadable extracellular matrix hydrogel features natural, biological components (derived from lung extracellular matrix), providing a lung-specific composition. FIG. 2B shows a schematic of the biomolecules 201 attached to a core-shell polymeric particle 202 to provide an extracellular matrix particle 203. FIG. 2C shows the particles 203 in the hydrogel-forming suspension. FIG. 2D is the same view as FIG. 2C with additional imaging to show the hydrogel matrix 204 surrounding the particles 203. FIG. 2E shows the particles in the hydrogel matrix layer 102. Also shown is the porous thermogel layer 103. FIG. 2F shows a cross-sectional view of the hydrogel matrix layer 102 applied to the lung surface 101.

A collagen-based gelation process allows for pleural adhesion and cell/particle access into the site of injury. The matrix hydrogel is able to be loaded with therapeutics (e.g., cells, exosomes, growth factors, drugs). It can be delivered directly onto the lung surface at the site of injury, bronchoscopically for endobronchial injuries, or through interventional radiology biopsy needles.

The tissue specific hydrogel comprises extracellular matrix components such that it may respond to the natural signaling and regulatory function from biophysical and biochemical cues. It may provide immunomodulatory effects from paracrine actions, episomal or microsomal particles. It may comprise antigen-presenting cells and allow for the transfer of mitochondria. Mesenchymal stem cells (MSCs) may facilitate tissue regeneration at the site of the leak.

FIG. 3 shows various aspects of the thermogel layer. A porous thermogel is subsequently applied to contain the therapeutic cargo at the site of air leaks and seal the damaged lung. As shown schematically in FIG. 3A, the porous thermogel comprises a mixture of three (3) components: (i) gelatin 301, (ii) transglutaminase 302, and (iii) extracellular matrix 303 components derived from lung, visceral pleura, and/or other connective tissues. Transglutaminase (TG) 302 crosslinks the gelatin particles desirably at a temperature at about human body temperature.

Figure 3A:
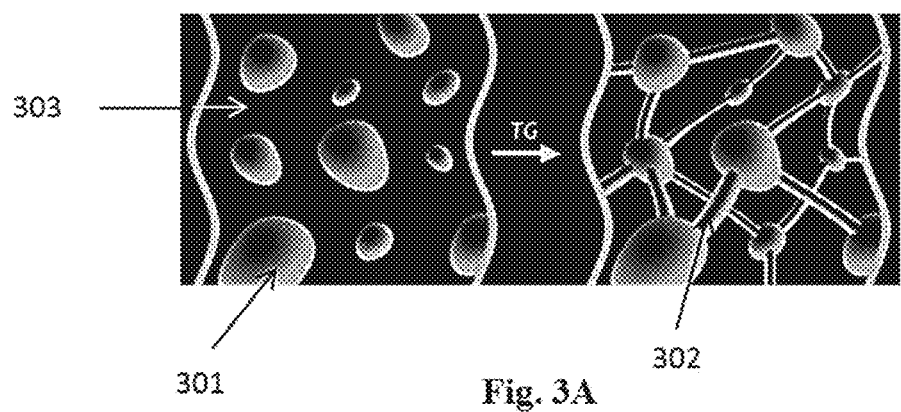
FIGS. 3A-3D show aspects of the thermogel layer.
Figure 3B:
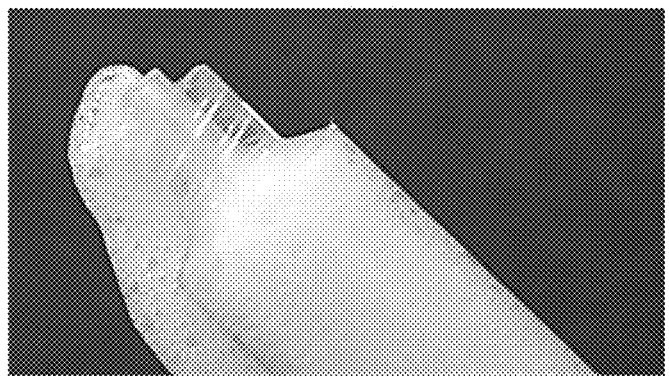
Figure 3D:
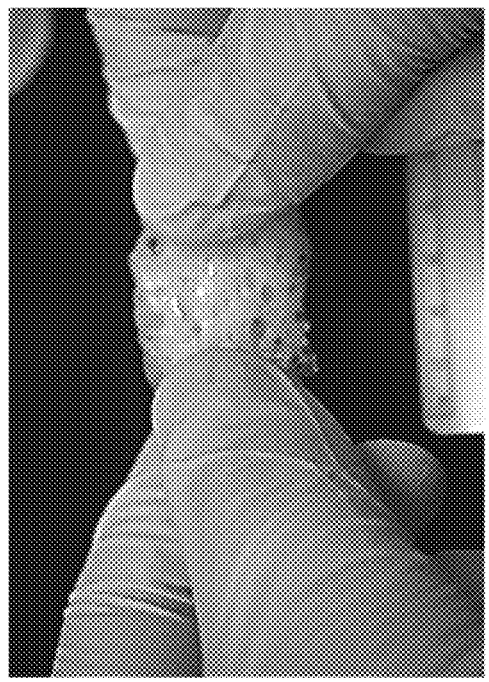
Figure 3C:
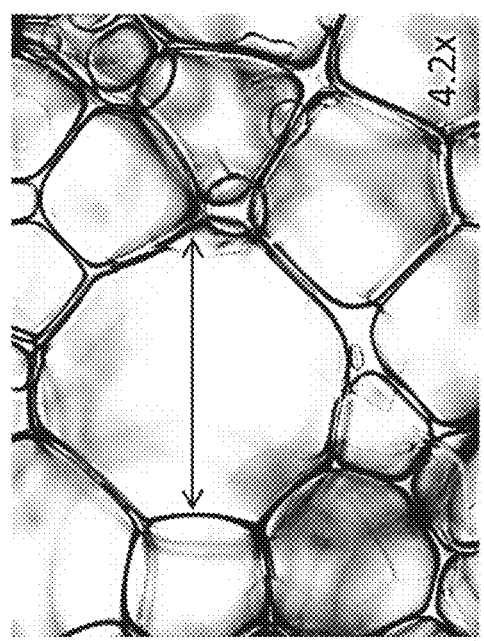

The porous thermogel patch features a porous structure that mimics native lung alveolar architecture. Its porosity is adjustable, and can be applied with a microfluidic bubble generator, as shown in FIG. 3B. FIG. 3C shows an enlarged view of the porous thermogel where the pores have an average diameter of 0.851 mm (std 0.2 mm). As shown in FIG. 3D, it flexible and elastic to allow it to biomechanically compliant to lung contraction and expansion during respiration, with elastic and tensile strength that allows for uniform surface load and minimizes potential for tearing and tissue damage (a problem with conventional sealants). The three-part composition provides rapid bonding, and the kinetics may be adjusted for a gelation set point at body temperature. The thermogel exhibits no antigenicity, and may treated to be bacteriostatic.

The biosealant system described herein provides improved ability to effectively seal pulmonary air leaks and superior biomechanics over prior sealant products. It also provides tissue healing facilitated by the therapeutic agents incorporated into the hydrogel matrix layer. Other advantages include little or no systemic toxicity and minimal local irritation.

Example 2

The therapeutic lung biosealant system can be applied as a prophylactic treatment during surgical lung resection or as a treatment for prolonged alveolar air leaks. For example, it may be applied to the external surface of the lung, e.g. on the visceral pleura, or through the airway for application to bronchial disruptions, e.g. bronchopleural fistulas. Alternatively, it may be applied as surface strips to stapling devices that would incorporate the bio-sealant directly along the staple line.

Figure 4B:
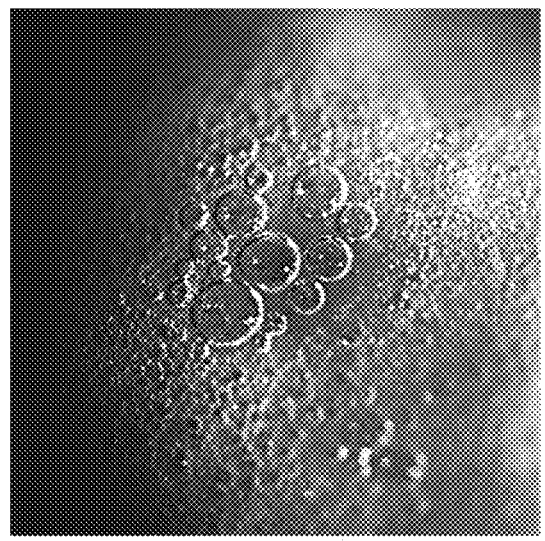
FIG. 4A shows a photograph of a puncture wound in lung tissue and FIG. 4B shows a photograph of the wound repaired with the biosealant described herein.
Figure 4A:
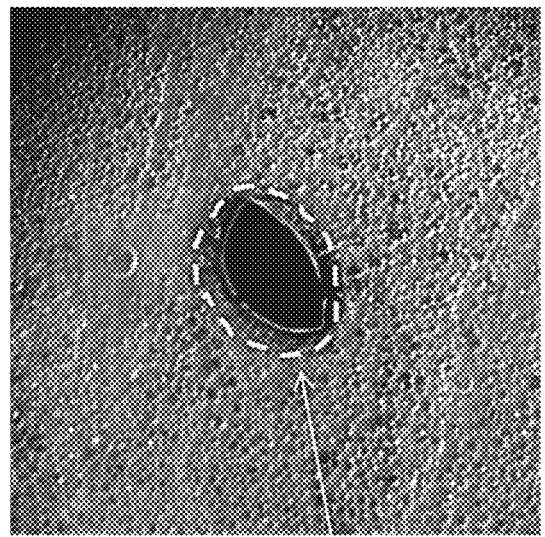

Referring to FIG. 4A, shown is a 16 gauge puncture wound 401 in lung tissue caused by a 16 gauge (1.65 mm diameter) needle outlined by the dashed line. FIG. 4B shows the wound repaired using the biosealant system described herein.

Example 3

Figure 5C:
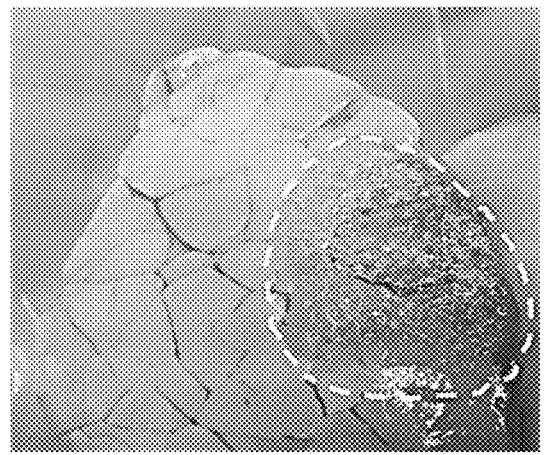
FIGS. 5A-5C show a parenchymal injury in lung tissue and the wound repaired with the biosealant described herein.
Figure 5B:
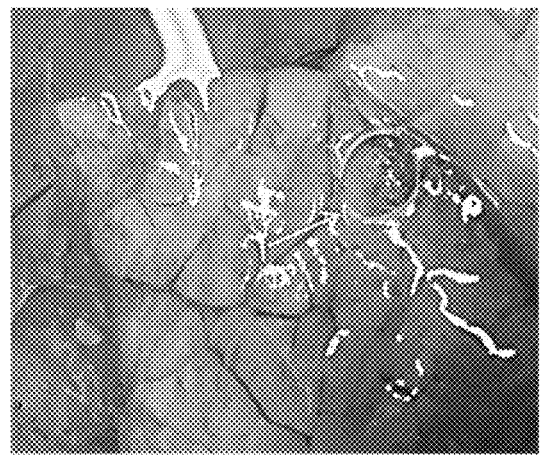
Figure 5A:
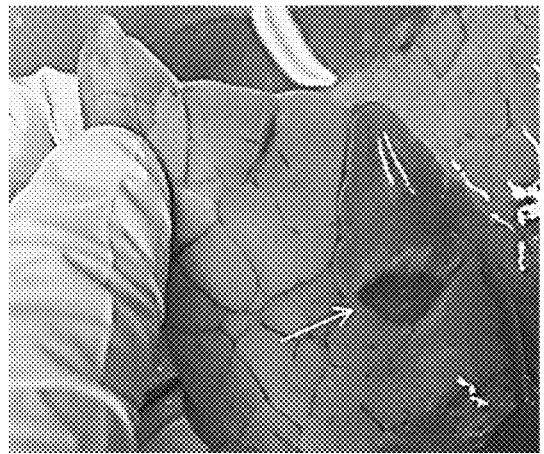

FIG. 5A shows a parenchymal injury (highlighted by arrow) in lung tissue and FIG. 5B shows the air leak resulting from the injury. FIG. 5C shows the wound repaired using the biosealant system (outlined by the dashed line) described herein.

The biosealant may also be used for ex-vivo lung repair, regeneration, bioengineering, and wound and burn healing.

Although described herein primarily for use in treating pulmonary air leaks, the biosealant system may be adapted for treatment of other organs by modification using cellular or extracellular components from other organs. For example, the biosealant with suitable modifications may be used for skin repair, treatment of alimentary tract leaks, and prophylactic sealing of other organs during surgical intervention.

While methods, systems and devices are described herein by way of examples and embodiments, those skilled in the art recognize that the methods, systems and devices for culturing tissue constructs are not limited to the embodiments or drawings described. It should be understood that the drawings and description are not intended to be limited to the particular form disclosed. Rather, the intention is to cover all modifications, equivalents and alternatives falling within the spirit and scope of the appended claims. Any headings used herein are for organizational purposes only and are not meant to limit the scope of the description or the claims. As used herein, the word "may" is used in a permissive sense (i.e., meaning having the potential to) rather than the mandatory sense (i.e., meaning must). Similarly, the words "include," "including," and "includes" mean including, but not limited to.

Having described and illustrated the principles of the disclosed subject matter with reference to the described embodiments, it will be recognized that the described embodiments can be modified in arrangement and detail without departing from such principles. It should be understood that the systems, devices, processes, or methods described herein are not related or limited to any particular type of environment, unless indicated otherwise.

In view of the many possible embodiments to which the principles of the disclosed subject matter can be applied, we claim as our disclosed subject matter all such embodiments as can come within the scope and spirit of the following claims and equivalents thereto.

What is claimed is:

1. A biosealant composition comprising an extracellular matrix hydrogel and a thermogel having pores, the pores having an average diameter of about 0.025 mm to about 0.90 mm;
   wherein the extracellular matrix hydrogel comprises a first extracellular matrix protein, an unbranched polysaccharide, and an elastic protein; and
   wherein the thermogel comprises a gelatinous material and a cross-linking enzyme in an amount sufficient to result in gelation of the thermogel at a temperature from about 35° C. to 37° C.

2. The biosealant composition of claim 1, wherein the first extracellular matrix protein is collagen, wherein the elastic protein is elastin, and wherein the unbranched polysaccharide is sulfated glycosaminoglycan.

3. The biosealant composition of claim 1, wherein the cross-linking enzyme is transglutaminase.

4. The biosealant composition of claim 1, wherein the extracellular matrix hydrogel also comprises additional therapeutics selected from the group consisting of: cells, microsomes, peptides, drugs and a combination thereof.

5. The biosealant composition of claim 1, wherein the cross-linking enzyme is present in an amount from about 0.5 units/mL to 5 units/mL.

6. The biosealant composition of claim 1, wherein the gelatinous material is gelatin.

7. The biosealant composition of claim 1, wherein the biosealant composition does not contain fibrin.

8. The biosealant composition of claim 1, wherein the first extracellular matrix protein is present in an amount from about 25% by weight to about 75% by weight of the total weight of the first extracellular matrix protein, unbranched polysaccharide, and elastic protein of the extracellular matrix hydrogel.

9. The biosealant composition of claim 1, wherein the unbranched polysaccharide is present in an amount from about 0.5% by weight to about 15% by weight of the total weight of the first extracellular matrix protein, unbranched polysaccharide, and elastic protein of the extracellular matrix hydrogel.

10. The biosealant composition of claim 1, wherein the elastic protein is present in an amount from about 25% by weight to about 75% by weight of the total weight of the first extracellular matrix protein, unbranched polysaccharide, and elastic protein of the extracellular matrix hydrogel.

11. A method of making the biosealant composition according to claim 1 comprising the steps of:
   mixing a first extracellular matrix protein, an unbranched polysaccharide, an elastic protein, and a first cross-linking enzyme to form an extracellular matrix hydrogel;
   mixing a gelatinous material in saline with a second cross-linking enzyme to form a thermogel;

heating the thermogel to about 52° C. to 55° C.; and
making the thermogel porous.

12. The method of claim 11, wherein the step of making the thermogel porous comprises applying a bubbling gas with a bubble generator through the thermogel.

13. The method of claim 11, wherein the first extracellular matrix protein is collagen, wherein the elastic protein is elastin, wherein the unbranched polysaccharide is sulfated glycosaminoglycan, and wherein the first and second cross-linking enzyme is transglutaminase.

14. A biosealant composition comprising an extracellular matrix hydrogel and a thermogel comprising a gelatinous material and a cross-linking enzyme in an amount sufficient to result in gelation of the thermogel at a temperature from about 35° C. to 37° C., wherein the thermogel has pores of average diameter of about 0.025 mm to 0.90 mm;
wherein the extracellular matrix hydrogel comprises a first extracellular matrix protein, an unbranched polysaccharide, and an elastic protein; and
wherein the extracellular matrix hydrogel comprises additional therapeutics selected from the group consisting of cells, microsomes, peptides, drugs and a combination thereof.

15. The biosealant composition of claim 14, wherein the cross-linking enzyme is transglutaminase.

16. The biosealant composition of claim 14, wherein the gelatinous material is gelatin.

17. The biosealant composition of claim 14, wherein the biosealant composition does not contain fibrin.

18. The biosealant composition of claim 14, wherein the first extracellular matrix protein is present in an amount from about 25% by weight to about 75% by weight of the total weight of the first extracellular matrix protein, unbranched polysaccharide, and elastic protein of the extracellular matrix hydrogel.

19. The biosealant composition of claim 14, wherein the unbranched polysaccharide is present in an amount from about 0.5% by weight to about 15% by weight of the total weight of the first extracellular matrix protein, unbranched polysaccharide, and elastic protein of the extracellular matrix hydrogel.

20. The biosealant composition of claim 14, wherein the elastic protein is present in an amount from about 25% by weight to about 75% by weight of the total weight of the first extracelluar matrix protein, unbranched polysaccharide, and elastic protein of the extracellular matrix hydrogel.

21. A biosealant composition comprising an extracellular matrix hydrogel comprising
a first extracellular matrix protein, an unbranched polysaccharide, and an elastic protein and
a thermogel comprising a gelatinous material and a cross-linking enzyme in an amount sufficient to result in gelation of the thermogel at a temperature from about 35° C. to 37° C.,
wherein the elastic protein is present in an amount from about 25% by weight to about 75% by weight of the total weight of the first extracellular matrix protein, unbranched polysaccharide, and elastic protein of the extracellular matrix hydrogel, and the thermogel has pores having an average diameter of about 0.025 mm to 0.90 mm.

22. The biosealant composition of claim 21, wherein the first extracellular matrix protein is collagen, wherein the elastic protein is elastin, and wherein the unbranched polysaccharide is sulfated glycosaminoglycan.

23. The biosealant composition of claim 21, wherein the cross-linking enzyme is transglutaminase.

24. The biosealant composition of claim 21, wherein the extracellular matrix hydrogel also comprises additional therapeutics selected from the group consisting of: cells, microsomes, peptides, drugs and a combination thereof.

25. The biosealant composition of claim 21, wherein the gelatinous material is gelatin.

26. The biosealant composition of claim 21, wherein the biosealant composition does not contain fibrin.

* * * * *